(12) United States Patent
Natarajan et al.

(10) Patent No.: US 7,667,042 B2
(45) Date of Patent: Feb. 23, 2010

(54) STABLE POLYMORPHIC FORMS OF AN ANTICONVULSANT

(75) Inventors: Muthukumaran Natarajan, Baroda (IN); Nileshkumar Sureshbhai Patel, Baroda (IN); Mehul Chandrakatbhai Bhatt, Baroda (IN); Srinivasu Kilaru, Baroda (IN); Rajamannar Thennati, Baroda (IN)

(73) Assignee: Sun Pharma Advanced Research Company Ltd., Andheri (E), Mumbai (IN)

( * ) Notice: Subject to any disclaimer, the term of this patent is extended or adjusted under 35 U.S.C. 154(b) by 197 days.

(21) Appl. No.: 10/583,805

(22) PCT Filed: Dec. 24, 2004

(86) PCT No.: PCT/IN2004/000447

§ 371 (c)(1),
(2), (4) Date: Jun. 22, 2006

(87) PCT Pub. No.: WO2005/122698

PCT Pub. Date: Dec. 29, 2005

(65) Prior Publication Data

US 2007/0066656 A1 Mar. 22, 2007

(30) Foreign Application Priority Data

Dec. 24, 2003 (IN) ............ 1210/MUM/2003

(51) Int. Cl.
*C07D 409/00* (2006.01)
(52) U.S. Cl. .................................. 546/212
(58) Field of Classification Search .............. None
See application file for complete search history.

(56) References Cited

U.S. PATENT DOCUMENTS

| 5,010,090 A | 4/1991 | Gronvald et al. |
| 5,354,760 A | 10/1994 | Petersen et al. |
| 5,958,951 A | 9/1999 | Ahrndt et al. |

OTHER PUBLICATIONS

Chawla et al., CRIPS vol. 5, No. 1, Jan.-Mar. 2004, p. 9-12.*
Newman et al., DDT vol. 8, Oct. 2003, p. 898-905.*
Byrn et al., "Solid-State Chemistry of Drugs", 1999, p. 62-63.*
Andersen et al. "The Synthseis of Novel GABA Uptake Inhibitors. 1.Elucidation of the Structure-Activity Studies Leading to the Choice of (R)-1-[4,4-Bis(3-methyl-2-thienyl)-3-butenyl]-3-piperidinecarboxylic Acid (Tiagabine) as an Anticonvulsant Drug Candidate" Journal of Medicinal Chemistry, 36 p. 1716-1725 (1993).

* cited by examiner

*Primary Examiner*—Golam M. M. Shameem
*Assistant Examiner*—Sun Jae Y Loewe
(74) *Attorney, Agent, or Firm*—Schwegman Lundberg & Woessner, P.A.

(57) ABSTRACT

Stable polymorphic forms III, IV and substantially amorphous form of an anticonvulsant, tiagabine hydrochloride.

3 Claims, 5 Drawing Sheets

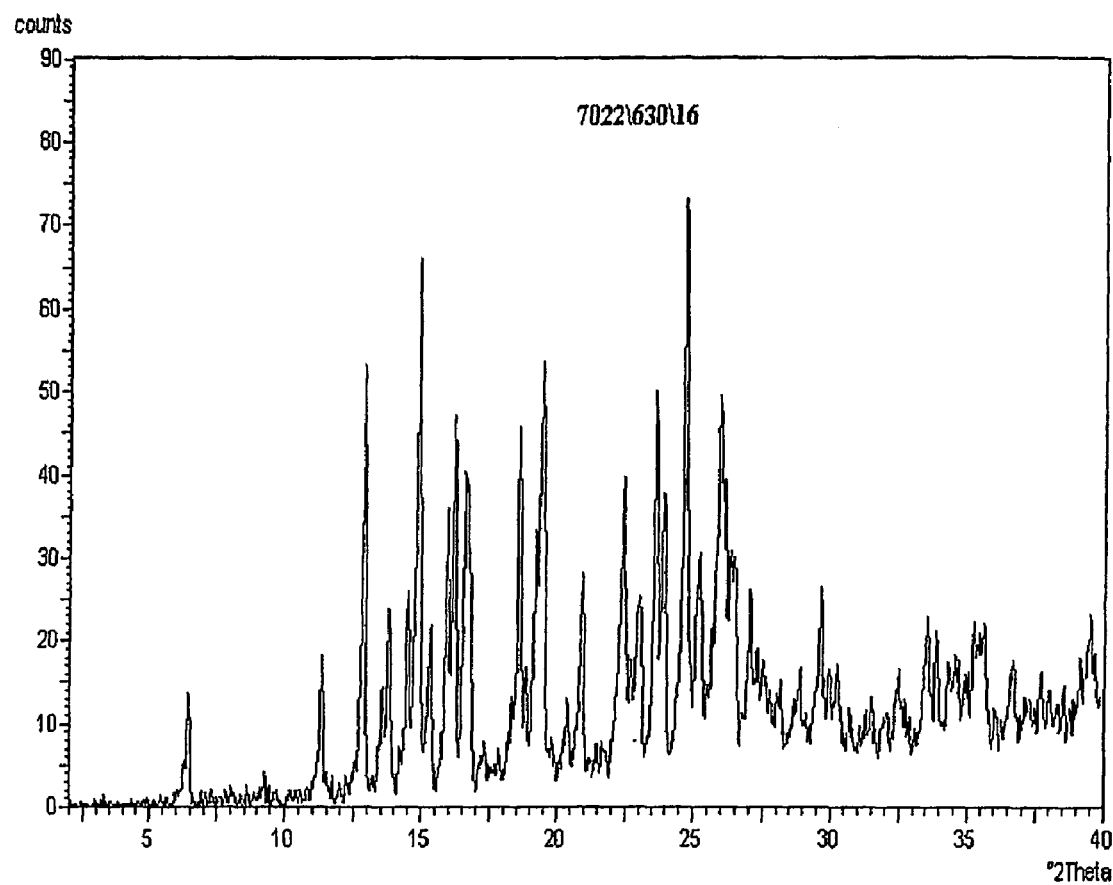
Fig. 1 : XRD PATTERN OF FORM III

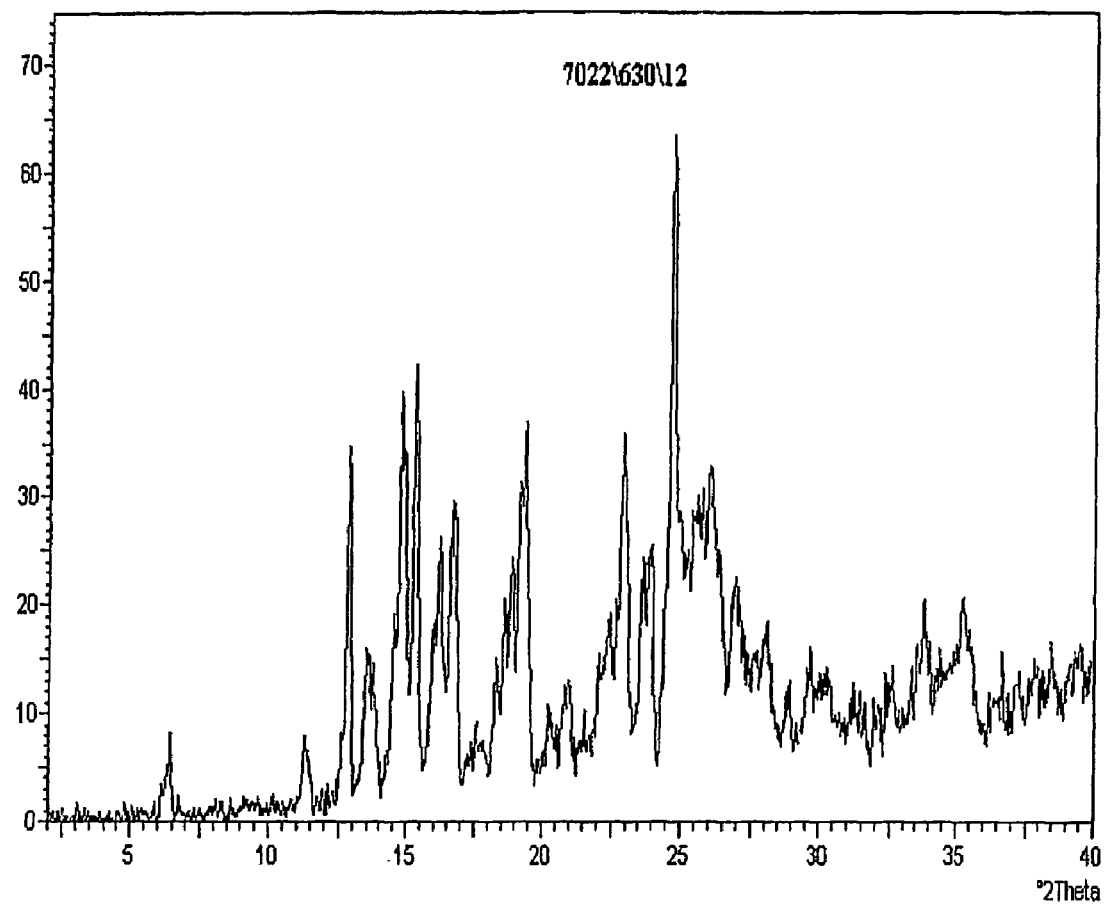
Fig. 2 : XRD PATTERN OF FORM IV

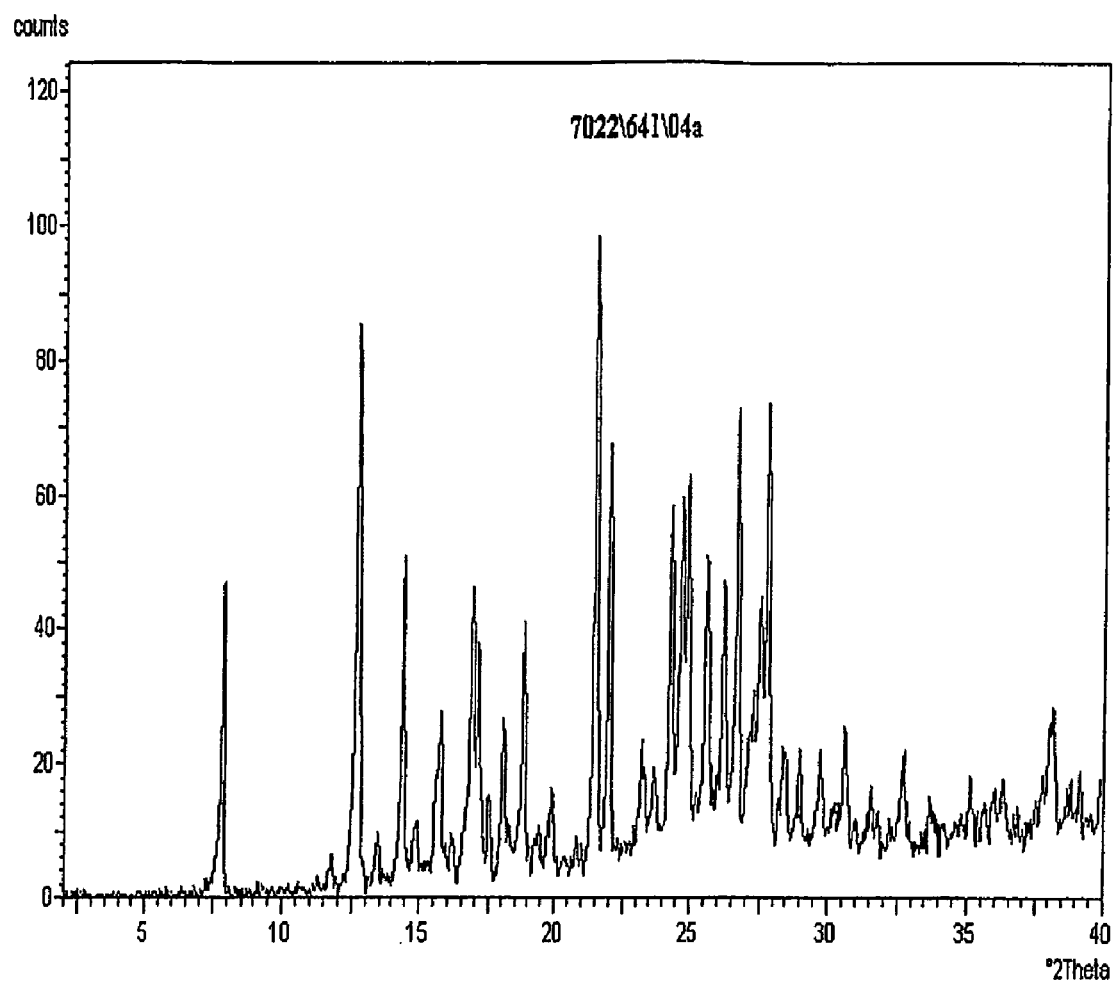
Fig.3: XRD PATTERN OF ACETONITRILE SOLVATE FORM

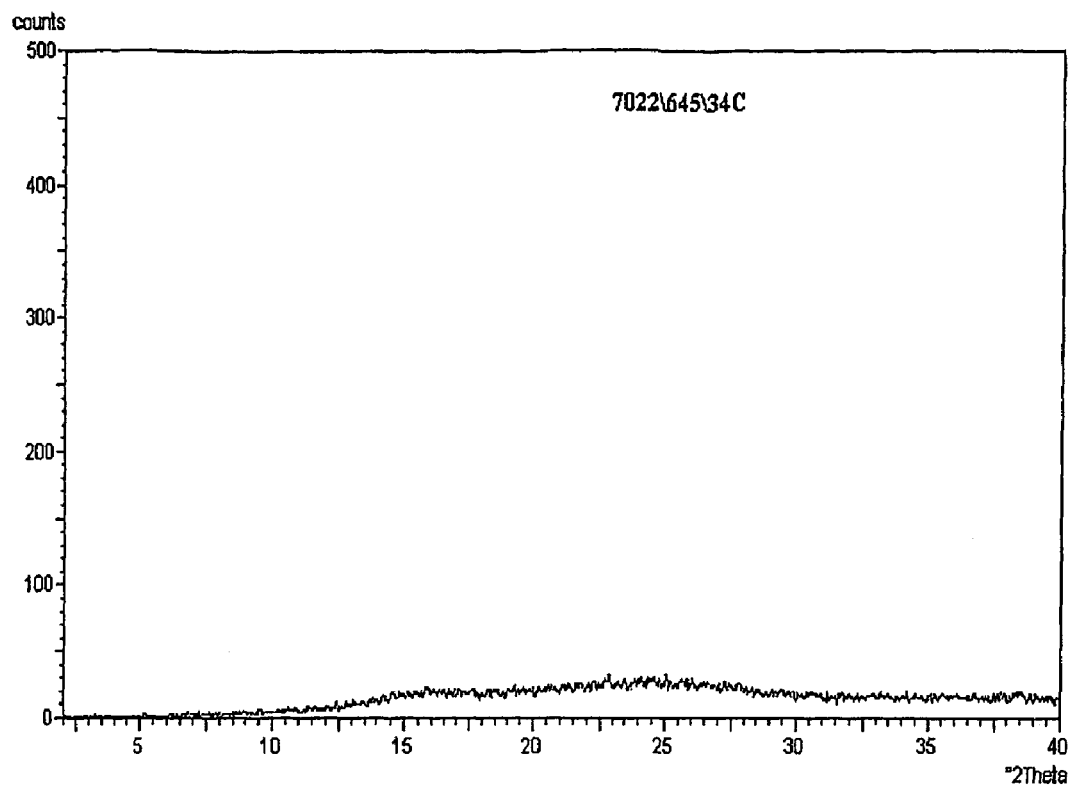
Fig. 4 : XRD PATTERN OF FORM V AMORPHOUS FORM (Prepared by spray drying method)

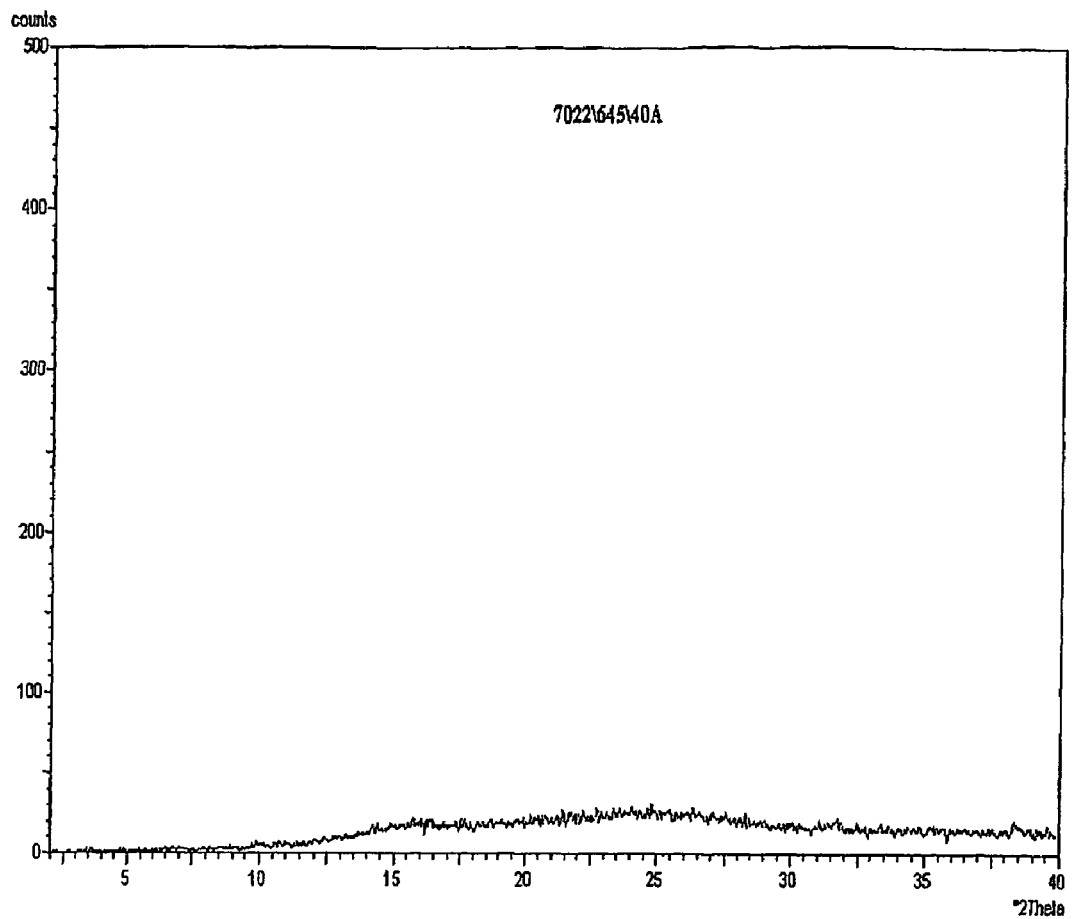
Fig. 5 : XRD PATTERN OF FORM V AMORPHOUS FORM (Prepared by freeze drying method)

STABLE POLYMORPHIC FORMS OF AN ANTICONVULSANT

The present invention relates to novel stable polymorphic forms of an anticonvulsant, tiagabine hydrochloride (INN name) used in the treatment of epilepsy.

BACKGROUND OF THE INVENTION

U.S. Pat. No. 5,010,090 (assigned to Novo Nordisk, referred to hereinafter as '090) discloses tiagabine hydrochloride and the process of its preparation. The process adopted herein is very laborious and expensive as it utilizes column chromatography for purification. Further, the product is crystallised using ethyl acetate, isopropanol, acetone or water yielding product contaminated with high levels of solvent. Use of alternative organic solvents such as acetonitrile, butylacetate, toluene, acetone, dichloromethane etc. also gives product containing various amounts of the used crystallization solvent. The crystallization solvents are unwanted as they affect the stability of pharmaceutical products and are toxic to humans. Further the product manufactured using ethylacetate and other organic solvents often forms clathrates, hence not usable as pharmaceutical material due to high levels of solvent contamination. This patent does not disclose the polymorphic form of tiagabine hydrochloride.

U.S. Pat. No. 5,354,760 (assigned to Novo Nordisk, referred to hereinafter as '760) patent provides monohydrate form of tiagabine hydrochlrodie referred to herein as form I. The monohydrate form of tiagabine hydrochloride is stable, non-hygroscopic and is suitable for pharmaceutical formulations as the only residual solvent in the product is water. However, it is reported that the monohydrate crystalline form is less stable at elevated temperature making its use inconvenient during formulation. The '760 patent discloses a process of preparation of form I tiagabine hydrochloride (monohydrate) comprising crystallization of tiagabine hydrochloride form an aqueous solution.

U.S. Pat. No. 5,958,951 (assigned to Novo Nordisk, referred to hereinafter as '951) claims anhydrous crystalline form of tiagabine hydrochloride referred to herein as form II. The product obtained was reported to be non-hygroscopic and thermally stable. The process for preparation of form II claimed in '951 was the same as the process disclosed in '760, however the examples differ with respect to the conditions of crystallization for example in the exemplified process of '951 the crystallization from aqueous solution may occur at high temperature of about 52° C. over a period of about 18 hours. Thus, the process for the preparation of anhydrous form is time consuming.

OBJECT OF THE INVENTION

The object of the present invention is to provide novel stable polymorphic forms III, IV and substantially amorphous form of tiagabine hydrochloride Another object is to provide novel solvate of tiagabine hydrochloride with acetonitrile.

Yet another object of the present invention is to provide processes for the preparation of novel polymorphic forms III, IV, novel solvate with acetonitrile and substantially amorphous form of tiagabine hydrochloride.

SUMMARY OF THE INVENTION

The present invention provides novel stable polymorphic forms of tiagabine hydrochloride, an anticonvulsant.

Particularly, the present invention provides novel stable polymorphic forms III and IV of tiagabine hydrochloride.

More particularly, the present invention provides stable polymorph IV of tiagabine hydrochloride that exhibits an X-ray powder diffraction pattern having characteristic peaks expressed in degrees 2 theta at about 13.6, 14.5, 15.4, 16.2, 16.8, 23.0, 24.7, 26.0

The present invention also provides tiagbine hydrochloride acetonitrile solvate.

The present invention also provides amorphous tiagbine hydrochloride.

The present invention also provides a process for the preparation of each of the polymorphic forms III and IV of tiagabine hydrochloride and amorphous tiagabine hydrochloride.

BRIEF DESCRIPTION OF THE DRAWINGS

FIG. 1 shows the X-ray diffraction pattern of tiagabine hydrochloride Form III.

FIG. 2 shows the X-ray diffraction pattern of tiagabine hydrochloride Form IV.

FIG. 3 shows the X-ray diffraction pattern of crystalline form of tiagabine hydrochloride acetonitrile solvate.

FIG. 4 shows the X-ray diffraction pattern of tiagabine hydrochloride Form V amorphous form prepared by spray drying.

FIG. 5 shows the X-ray diffraction pattern of tiagabine hydrochloride Form V amorphous form prepared by freeze drying.

DETAILED DESCRIPTION OF THE INVENTION

When we followed the claimed process of the '951 patent i.e. by dissolving tiagabine hydrochloride in an aqueous hydrochloric acid solution, and precipitating tiagabine hydrochloride from the aqueous hydrochloric acid solution we obtained the anhydrous form II and on analysis found that the cell parameters of the form II were:

$a=7.775(7)Å\ \alpha=78.38(9)°$ $b=11.10(1)Å\ \beta=75.88(8)°$ $c=14.33(2)Å\ \gamma=89.21(9)°$ $Vol=1173.96Å^3$ We studied the solubility of tiagabine hydrochloride in various organic solvents and found that tiagabine hydrochloride has limited solubility in various organic solvents compared to that in water. The solubility data is given in Table-1.

TABLE 1

SOLUBILITY DATA OF TIAGABINE HYDROCHLORIDE AT ROOM TEMPERATURE

| S. NO | SAMPLE QUANTITY | SOLVENT | VOLUME OF |
|---|---|---|---|
| 1 | 100 mg | Toluene | >100 ml |
| 2 | 100 mg | DMF | 0.5 ml |
| 3 | 100 mg | Ethylacetate | >100 ml |
| 4 | 100 mg | Acetone | 24 ml |
| 5 | 100 mg | Methanol | 0.2 ml |
| 6 | 100 mg | Ethanol | 0.3 ml |
| 7 | 100 mg | IPA | 1.3 ml |
| 8 | 100 mg | Acetonitrile | >100 ml |
| 9 | 100 mg | Water | 0.7 ml |

Further, whereas the prior art method of crystallization from aqueous solution was item consuming we found that process using crystallization from organic solvents was rapid and resulted in high yields.

The stable polymorphic form III of tiagabine hydrochloride exhibits an x-ray diffraction pattern as depicted in FIG. 1.

The stable polymorphic form IV of tiagabine hydrochloride exhibits an x-ray diffraction pattern as depicted in FIG. 2.

According to one embodiment of the present invention novel stable polymorphic forms of tiagabine hydrochloride may be made available which are stable. Preferably, polymorphic forms III, IV and acetonitrile solvate of tiagabine hydrochloride.

The stable polymorph IV of tiagabine hydrochloride exhibits an X-ray powder diffraction pattern having characteristic peaks expressed in degrees 2 theta at approximately 13.6, 14.5, 15.4, 16.2, 16.8, 23.0, 24.7. Preferably, x-ray powder diffraction pattern having characteristic peaks expressed in degrees 2 theta at about 4.46, 5.03, 5.48, 6.46, 7.46, 8.11, 8.35, 9.45, 10.29, 11.41, 11.94, 12.32, 12.91, 13.59, 13.83, 14.52, 14.85, 15.36, 15.97, 16.26, 16.83, 17.85, 18.36, 18.59, 18.85, 19.25, 19.45, 20.36, 20.98, 21.59, 22.15, 22.49, 22.99, 23.67, 23.96, 24.75, 25.33, 25.62, 25.97, 26.43, 27.02, 27.48, 27.94, 28.16, 28.88, 29.63, 30.27, 30.87, 31.54, 32.11, 32.52, 32.96, 33.52, 33.89, 34.45, 35.33, 35.59, 36.02, 36.53, 36.77, 37.28, 37.75, 38.24, 39.12.

More preferably, the stable polymorph IV of tiagabine hydrochloride exhibits x-ray powder diffraction pattern as given below:

| °2θ | % Relative Intensity |
|---|---|
| 4.4552 | 1.19 |
| 5.0280 | 1.57 |
| 5.4800 | 1.40 |
| 6.4618 | 26.01 |
| 7.4555 | 1.14 |
| 8.1120 | 1.05 |
| 8.3469 | 0.55 |
| 9.4458 | 1.10 |
| 10.2976 | 0.07 |
| 11.4113 | 10.74 |
| 11.9400 | 0.48 |
| 12.3205 | 0.54 |
| 12.9051 | 73.52 |
| 13.5866 | 34.36 |
| 13.8336 | 22.44 |
| 14.5237 | 21.87 |
| 14.8525 | 56.45 |
| 15.3566 | 100.00 |
| 15.9704 | 19.58 |
| 16.2550 | 37.61 |
| 16.8324 | 58.66 |
| 17.8470 | 3.19 |
| 18.3616 | 8.99 |
| 18.5960 | 9.64 |
| 18.8520 | 23.20 |
| 19.2462 | 43.35 |
| 19.4466 | 35.71 |
| 20.3582 | 7.12 |
| 20.9813 | 10.55 |
| 21.5955 | 2.40 |
| 22.1478 | 7.55 |
| 22.4936 | 13.01 |
| 22.9961 | 37.54 |
| 23.6666 | 13.88 |
| 23.9563 | 22.03 |
| 24.7460 | 64.16 |
| 25.3288 | 14.29 |
| 25.6240 | 16.37 |
| 25.9657 | 16.05 |
| 26.4322 | 8.81 |

-continued

| °2θ | % Relative Intensity |
|---|---|
| 27.0201 | 8.24 |
| 27.4772 | 2.36 |
| 27.9365 | 4.32 |
| 28.1570 | 6.49 |
| 28.8818 | 3.13 |
| 29.6343 | 3.57 |
| 30.2723 | 3.56 |
| 30.8721 | 0.87 |
| 31.5401 | 1.93 |
| 32.1129 | 0.31 |
| 32.5239 | 2.94 |
| 32.9663 | 1.20 |
| 33.5206 | 2.07 |
| 33.8931 | 5.86 |
| 34.4505 | 1.63 |
| 35.3347 | 6.23 |
| 35.5891 | 4.77 |
| 36.0204 | 0.29 |
| 36.5288 | 0.90 |
| 36.7720 | 0.81 |
| 37.2771 | 1.76 |
| 37.7485 | 0.72 |
| 38.2364 | 0.52 |
| 39.1197 | 1.45 |

Stable polymorph IV of tiagabine hydrochloride exhibits unit cell parameters as given below:

$a=10.788(3)$Å $\alpha=97.65(2)°$ $b=11.492(2)$Å $\beta=108.92(2)°$ $c=14.799(4)$Å $\gamma=101.86(2)°$ Vol=1658.63 Å$^3$ In embodiment of the present invention the stable polymorph IV of tiagabine hydrochloride may be obtained in particle size with volume mean diameter (VMD) less than 20 microns. There is no change in the x-ray diffraction pattern of stable polymorph IV of tiagabine hydrochloride after standing for 6 months under ambient conditions.

The process for the preparation of the novel stable polymorphic forms III or IV of tiagabine hydrochloride of the present invention comprises dissolving tiagabine hydrochloride to an organic solvent or a mixture of organic solvent and organic anti-solvent and adding a sufficient amount of organic non-solvent to the solution to cause crystallization at a selected temperature wherein the selected temperature is such that form IV of tiagabine hydrochloride is crystallized. The organic solvent may be water miscible or water immiscible. Water miscible organic solvent may be used alone or in admixture with water.

In accordance with another embodiment of the present invention, there is provided a process for the preparation of novel stable polymorphic form III and form IV of tiagabine hydrochloride.

A process for the preparation of the novel stable polymorphic form IV of tiagabine hydrochloride comprises dissolving tiagabine hydrochloride in an organic solvent or a mixture of organic solvent and an organic non-solvent and adding a sufficient amount of organic anti-solvent to the solution to cause crystallization at a selected temperature wherein the selected temperature is such that form IV of tiagabine hydrochloride is crystallized preferably the selected temperature may be 35+ or −10° C. The solution may be optionally cooled at 0° to 10° C. for further crystallization.

The novel stable polymorphic form IV of tiagabine hydrochloride may also be prepared by crystallizing crystallizing tiagabine hydrochloride from a solution of tiagabine hydrochloride in an organic solvent or a mixture of organic solvent and organic anti-solvent wherein the solution is seeded with tiagabine hydrochloride form IV seed crystals.

A process for the preparation the novel stable polymorphic form III of tiagabine hydrochloride comprises adding tiagabine hydrochloride in an organic solvent, heating to dissolve and adding sufficient amount of organic anti-solvent to cause crystallization at a selected temperature wherein the selected temperature is such that form III of tiagabine hydrochloride is crystallized.

The novel stable polymorphic form III of tiagabine hydrochloride may also be prepared by crystallizing tiagabine hydrochloride from a solution of tiagabine hydrochloride in an organic solvent or a mixture of organic solvent and organic anti-solvent wherein the solution is seeded with tiagabine hydrochloride form III seed crystals.

The organic solvent may be selected from the group consisting of aliphatic or aromatic or cyclic hydrocarbon such as n-pentane, n-hexane, n-octane, cyclohexane, toluene and the like; halogenated aliphatic or aromatic hydrocarbons such as dichloromethane, chlorobenzene; alkanols such as methanol, ethanol, t-butanol, isopropanol, cyclohexanol and the like; ethers such as diethylether, tetrahydrofuran, dioxane; ketones such as acetone, methylethylketone, cyclohexanone; nitriles such as acetonitrile; amides such as dimethylformamide, dimethylacetamide and the like; esters such as ethylacetate, butylacetate; sulfoxides such as dimethylsulfoxide and the like; water and mixtures thereof.

The preferred organic solvents used are polar aprotic organic solvents such as dimethylformamide or dimethylsulfoxide. The preferred organic anti-solvent is toluene.

The dissolution of tiagabine hydrochloride in solvent(s) may be carried out at ambient or at elevated temperatures.

In a preferred embodiment of the invention, the novel stable polymorphic form IV of tiagabine hydrochloride is prepared by dissolving tiagabine hydrochloride in a mixture of dimethylformamide and toluene, followed by adding sufficient quantity of toluene to the resulting solution at room temperature.

In another preferred embodiment of the invention, the novel stable polymorphic form III of tiagabine hydrochloride is prepared by adding tiagabine hydrochloride to dimethylformamide, heating to dissolve and adding sufficient amount of toluene to cause crystallization at a temperature ranging from 50 to 55° C.

Isolation of the novel polymorphic forms III or IV may be achieved by using techniques such as filtration/centrifugation and drying. Filtration may be carried out in the presence or absence of vacuum. Drying may be carried out at ambient or elevated temperature in the presence or absence of vacuum. The product may be dried using different techniques such as fluid bed drying, tray drying, spray freeze drying and rotatory drying techniques with or without application of vacuum and/or under inert conditions.

The new polymorphic forms III and IV of tiagabine hydrochloride are suitable for pharmaceutical formulations.

The organic solvent may be selected from the group consisting of aliphatic or aromatic or cyclic hydrocarbon such as n-pentane, n-hexane, n-octane, cyclohexane, toluene and the like; halogenated aliphatic or aromatic hydrocarbons such as dichloromethane, chlorobenzene; alkanols such as methanol, ethanol, t-butanol, isopropanol, cyclohexanol and the like; ethers such as diethylether, tetrahydrofuran, dioxane; ketones such as acetone, methylethylketone, cyclohexanone; nitriles such as acetonitrile; amides such as dimethylformamide, dimethylacetamide and the like; esters such as ethylacetate, butylacetate; sulfoxides such as dimethylsulfoxide and the like; water and mixtures thereof.

The dissolution of tiagabine hydrochloride in solvent(s) may be carried out at ambient or at elevated temperatures.

Crystallization of tiagabine hydrochloride from the solution may be carried out at ambient or lower temperatures. Crystallization may be allowed to occur by chilling or seeding or scratching the glass of the reaction vessel or cooling and other such common techniques. Isolation of the novel polymorphic forms may be achieved by using techniques such as filtration/centrifugation and drying. Filtration may be carried out in the presence or absence of vacuum. Drying may be carried out at ambient or elevated temperature in the presence or absence of vacuum. The product may be dried using different techniques such as fluid bed drying, tray drying, spray freeze drying and rotatory drying techniques with or without application of vacuum and/or under inert conditions.

For instance, polymorphic forms III or IV of tiagabine hydrochloride may be prepared by dissolving in polar aprotic solvent such as dimethylformamide or dimethylsulfoxide and the like. The dissolution may be carried out at ambient or higher temperature This is followed by addition of anti-solvent selected from aliphatic or aromatic hydrocarbon solvents such as hexane, heptane, cyclohexane, cycloheptane, benzene, toluene, xylene and the like to crystallize polymorphic forms III or IV within about 3 hrs at ambient or lower temperature, preferably −10 to 30° C.

The new polymorphic forms III and IV of tiagabine hydrochloride are suitable for pharmaceutical formulations.

According to yet another embodiment of the present invention of tiagabine hydrochloride acetonitrile solvate may be obtained, preferably crystalline tiagabine hydrochloride acetonitrile solvate. Crystalline form of tiagabine hydrochloride acetonitrile solvate is stable and isolable in good yields.

Crystalline form of tiagabine hydrochloride acetonitrile solvate exhibits an X-ray powder diffraction pattern having characteristic peaks expressed in degrees 2 theta at approximately 7.9, 21.5, 22.0, 24.3, 24.9, 26.7, 27.8.

Crystalline form of tiagabine hydrochloride acetonitrile solvate exhibits an x-ray diffraction pattern as depicted in FIG. 3.

According to another embodiment of the present invention substantially amorphous tiagabine hydrochloride may be made available.

Amorphous tiagabine hydrochloride may be prepared by various methods such as spray drying solution comprising tiagabine hydrochloride or freeze drying solution comprising tiagabine hydrochloride and the like XRD analysis of amorphous tiagabine hydrochloride as prepared by spray drying and freeze drying are as given in FIGS. 4 and 5.

The process for the preparation of tiagabine hydrochloride acetonitrile solvate comprising dissolving in acetonitrile or mixture comprising acetontrile and crystallizing by cooling or standing at ambient temperature.

We have also found that the solvates of tiagabine hydrochloride can also be employed for making the new forms for eg. stable acetonitrile solvate having 1 mole of acetonitrile when dried at 85-90° C. under vacuum yields form III of tiagabine hydrochloride.

The polymorphic forms III, IV, acetonitrile solvate and amorphous form of tiagabine hydrochloride are obtained from organic solvents or from drying of the solvates and had solvent levels below the acceptable limits, meeting ICH requirements. The data was reported in Table-2.

TABLE 2

RESIDUAL SOLVENT DATA

| S. no | Exp. No. | Form | Solvent(s) used | Solvent content | Limits as |
|---|---|---|---|---|---|
| 1. | 630/12 | IV | DMF+ | Not detected | NMT 880 |
| 2 | 630/16 | III | DMF+ | Not detected | NMT 880 |
| 2. | 630/37$_a$ | I | ETHYLACETA | Not detected | NMT 5000 |
| 3. | 630/37$_b$ | IV | ISOPROPANOL | 10 ppm | NMT 5000 |
| 4. | 630/37$_c$ | IV | ACETONE | 556 ppm | NMT 5000 |
| 5. | 616/20B | IV | METHANOL+ | Not detected | NMT 3000 |
| 6 | 641/04a | Acetonitrile | ACETONITRIL | Not detected | NMT 410 |

Stable polymorphic forms III, IV and amorphous forms are substantially free of solvent.

The invention is further illustrated but not restricted by the description in the following examples.

EXAMPLES

Example 1

Form-III of Tiagabine Hydrochloride 66 gm of tiagabine hydrochloride is dissolved in 135 ml DMF at 60-70° C. and the solution filtered. 1200 ml toluene is added to DMF solution containing tiagabine hydrochloride at 50-55° C. for a period of 15 min and the mixture is gradually cooled to room temperature in 1 hr period and further cooled to 0-5° C. and maintained at 0-5° C. for 1.5 hr. The material is filtered and washed with 150 ml toluene. Dried the material at 50-55° C. till LOD comes to less than 0.5%.

X-ray powder diffraction pattern having characteristic peaks expressed in degrees 2 theta at 6.4617, 9.3296, 11.3101, 12.9202, 13.7893, 14.4799, 14.9003, 15.3375, 15.9390, 16.2009, 16.5963, 16.7774, 18.5875, 19.4396, 20.3969, 22.4225, 23.0653, 23.6163, 23.9868, 24.6971, 25.2271, 25.9469, 26.4799, 27.0214, 27.2297, 28.8106, 29.6048, 31.4648, 32.4574, 33.5262, 33.8443, 35.6166, 36.6730.

Example 2(a)

Form-IV of Tiagabine Hydrochloride 650 gm of tiagabine hydrochloride is dissolved in 1.5 lit DMF at 70-80° C., and added to 6.5 lit toluene at room temperature for a period of 30 min and the mixture is gradually cooled to room temperature in 30 min time and further cooled to 5-10° C. in 30 min time and maintained at 5-10° C. for 2 hrs. The material is filtered and washed with 1.3 lit toluene. Dried the material at 55-58° C. till LOD comes to less than 0.5%. (LOD Result 0.1%).

XRD analysis of form IV after 6 months storage at ambient conditions, matches the XRD of '0' day sample.

X-ray powder diffraction pattern of this product exhibited characteristic peaks expressed in degrees 2 theta 4.1162, 4.9336, 6.4616, 6.9249, 8.0731, 9.3211, 10.3290, 11.3203, 11.5021, 12.3275, 12.8948, 13.5577, 13.8687, 14.5032, 14.7572, 14.9428, 15.3449, 15.9370, 16.2314, 16.3377, 16.6598, 16.8500, 17.3261, 17.3037, 17.8229, 18.3380, 18.6349, 18.8832, 19.1816, 19.4174, 19.8286, 20.3221, 20.9559, 21.2182, 21.6159, 22.1136, 22.4293, 22.9777, 23.6307, 23.9568, 24.3669, 24.7233, 24.9424, 25.2110, 25.5718, 25.9348, 26.1401, 26.5171, 26.8243, 27.0467, 27.5428, 27.9526, 28.1313, 28.6444, 28.8638, 29.5891, 29.9740, 30.3277, 30.7402, 31.4942, 32.0050, 32.4651, 32.9536, 33.5620, 33.9135, 34.4093, 35.2921, 365.7069, 36.8032, 37.2098, 37.8744, 39.0016, 39.2218, 39.6847.

Particle Size Analysis (Analysed by HELOS (H1551) & RODOS)

Form IV of tiagabine hydrochloride exhibited VMD=16.7 and 19.8 microns for 2 batches.

Form I of tiagabine hydrochloride exhibited VMD=60.2 microns.

Example 2(b)

Form-IV of Tiagabine Hydrochloride

Charge filtered 2 parts by volume (w.r.t weight of crude tiagabine hydrochloride) of Dimethylformamide in to the RBF between 28° C.~32° C. Charge filtered 2 parts by volume (w.r.t weight of crude tiagabine hydrochloride) of Toluene in to the RBF between 28° C.~32° C. Start stirring & charge crude tiagabine hydrochloride into the RBF between 28° C.~32° C. Stir the content for 10 min. between 28° C.~32° C. in the RBF to get uniform slurry. Heat the content to 65° C.~70° C. into RBF to get a clear solution.

Charge filtered 18 parts by volume of toluene (w.r.t weight of crude tiagabine hydrochloride) into reaction mixture between 65° C.~70° C. under stirring. Gradually cool the content between 28° C.~32° C. Stir the content for 45~60 min. between 28° C.~32° C. in the RBF. Further cool the content between 0° C.~5° C. Stir the content for 40 to 60 min. between 0° C.~5° C. in the RBF. Filter the product between 0° C.~5° C. through centrifuge. Spin dry product for 30 mins. Wash the cake twice with chilled toluene. Spin dry the product for 60 mins.

X-ray powder diffraction pattern of this product exhibited characteristic peaks expressed in degrees 2 theta at 4.4552, 5.0280, 5.4800, 6.4618, 7.4555, 8.1120, 8.3469, 9.4458, 10.2976, 11.4113, 11.9046, 12.3205, 12.9051, 13.5866, 13.8336, 14.5237, 14.8525, 15.3566, 15.9704, 16.2550, 16.8324, 17.8470, 18.3616, 18.5960, 18.8520, 19.2462, 19.4466, 20.3582, 20.9813, 21.5955, 22.1478, 22.4936, 22.9961, 23.6666, 23.9563, 24.7460, 25.3288, 25.6240, 25.9657, 26.4322, 27.0201, 27.4772, 27.9365, 28.1570, 28.8818, 29.6343, 30.2723, 30.8721, 31.5401, 32.1129, 32.5239, 32.9663, 33.5206, 33.8931, 34.4505, 35.3347, 35.5891, 36.0204, 36.5288, 36.7720, 37.2771, 37.7485, 38.2364, 39.1197.

Example 3

Amorphous Form of Tiagabine Hydrochloride 25 gm tiagabine hydrochloride is dissolved in 125 ml methanol +water mixture in 1:1 ratio at room temperature and spray dried the material at 45-50° C. It can also be prepared by dissolving 25 gm tiagabine hydrochloride in 175 ml water at 50-55° C. temperature and spray dried the material at 60° C. Another method of preparing amorphous form is by dissolving 10 gm tiagabine hydrochloride in 110 ml distilled water at room temperature and freeze dried the material for 24 hrs. XRD analysis are given in FIG. 4.

Example 4

Monoacetonitrile Solvate of Tiagabine Hydrochloride 5 gm of tiagabine hydrochloride is dissolved in 5 ml of methanol at 50-55° C., 50 ml acetonitrile is added to the methanol solution at 40-55° C. and cooled to room temperature in 1 hr period and further cooled to 5-10° C. and stirred for 2 hrs. Allowed the product to settle down and decanted the clear liquid. 50 ml ethyl acetate is added to the solid mass and stirred at 5-10° C. for 30 min, allowed the product to settle down the and decanted the clear liquid. Once again 50 ml ethyl acetate is added to the solid mass and stirred at 5-10° C. for 30 min, allowed the product to settle down the and decanted the clear liquid and dried the product mass in rotavapour under mild vaccum at 50° C. for 2 hrs.

The obtained acetonitrile solvate form was dried at 85-90° C. under vacuum to obtain form III of tiagabine hydrochloride.

X-ray powder diffraction pattern having characteristic peaks expressed in degrees 2 theta at 7.8620, 11.7636, 12.7349, 13.4762, 14.3981, 14.8732, 15.7568, 16.8937, 17.1116, 17.4938, 18.0955, 18.8451, 19.8842, 21.5213, 22.0078, 23.2299, 23.6888, 24.2776, 24.6823, 24.9106, 25.6034, 26.2117, 26.6924, 27.5132, 27.7983, 28.4213, 28.9876, 29.7388, 30.1996, 30.5997, 31.5065, 31.5065, 32.7371, 36.1356, 38.1619.

We claim:

1. Polymorph IV of tiagabine hydrochloride that exhibits an X-ray powder diffraction pattern having characteristic peaks expressed in degrees 2 theta at 13.6, 14.5, 15.4, 16.2, 16.8, 23.0, 24.7, 26.0, and exhibits unit cell parameters as follows:

$a$=10.788(3)Å  $\alpha$=97.65(2)°

$b$=11.492(2)Å  $\beta$=108.92(2)°

$c$=14.799(4)Å  $\gamma$=101.86(2)°

Vol=1658.63 Å3.

2. Polymorph IV of tiagabine hydrochloride that exhibits an X-ray powder diffraction pattern having characteristic peaks expressed in degrees 2 theta at 4.46, 5.03, 5.48, 6.46, 7.46, 8.11, 8.35, 9.45, 10.29, 11.41, 11.94, 12.32, 12.91, 13.59, 13.83, 14.52, 14.82, 14.85, 15.36, 15.97, 16.26, 16.83, 17.85, 18.36, 18.59, 18.85, 19.25, 19.45, 20.36, 20.98, 21.59, 22.15, 22.49, 22.99, 23.67, 23.96, 24.75, 25.33, 25.62, 25.97, 26.43, 27.02, 27.48, 27.94, 28.16, 28.88, 29.63, 30.27, 30.87, 31.54, 32.11, 32.52, 32.96, 33.52, 33.89, 34.45, 35.33, 35.59, 36.02, 36.53, 36.77, 37.28, 37.75, 38.24, 39.12.

3. The tiagabine hydrochloride Polymorph IV of claim 1 having a particle size with volume mean diameter less than 20 microns.

* * * * *

UNITED STATES PATENT AND TRADEMARK OFFICE
CERTIFICATE OF CORRECTION

| | | |
|---|---|---|
| PATENT NO. | : 7,667,042 B2 | Page 1 of 1 |
| APPLICATION NO. | : 10/583805 | |
| DATED | : February 23, 2010 | |
| INVENTOR(S) | : Muthukumaran Natarajan et al. | |

It is certified that error appears in the above-identified patent and that said Letters Patent is hereby corrected as shown below:

On the title page, in field (54), in "Title", in column 1, line 1, before "STABLE" insert -- NOVEL --.

In column 1, line 1, before "STABLE" insert -- NOVEL --.

Signed and Sealed this

Twenty-fifth Day of May, 2010

David J. Kappos
*Director of the United States Patent and Trademark Office*

UNITED STATES PATENT AND TRADEMARK OFFICE
CERTIFICATE OF CORRECTION

| | |
|---|---|
| PATENT NO. | : 7,667,042 B2 |
| APPLICATION NO. | : 10/583805 |
| DATED | : February 23, 2010 |
| INVENTOR(S) | : Muthukumaran Natarajan et al. |

It is certified that error appears in the above-identified patent and that said Letters Patent is hereby corrected as shown below:

Title Page.

Item [54], Title, the word "NOVEL" (as inserted by Certificate of Correction issued May 25, 2010) should be deleted and title is to be reinstated to read
-- STABLE POLYMORPHIC FORMS OF AN ANTICONVULSANT --.

Signed and Sealed this

Twenty-second Day of June, 2010

David J. Kappos
*Director of the United States Patent and Trademark Office*

UNITED STATES PATENT AND TRADEMARK OFFICE
CERTIFICATE OF CORRECTION

PATENT NO.      : 7,667,042 B2                                                              Page 1 of 1
APPLICATION NO. : 10/583805
DATED           : February 23, 2010
INVENTOR(S)     : Natarajan et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 443 days.

Signed and Sealed this

Twenty-eighth Day of December, 2010

David J. Kappos
*Director of the United States Patent and Trademark Office*